US010154997B2

(12) United States Patent
Marshall et al.

(10) Patent No.: US 10,154,997 B2
(45) Date of Patent: Dec. 18, 2018

(54) TREATMENT OF PARASITIC DISEASES USING KDAC INHIBITOR COMPOUNDS

(71) Applicant: Washington University, St. Louis, MO (US)

(72) Inventors: Garland R. Marshall, Clayton, MO (US); Makedonka Mitreva, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 15/228,802

(22) Filed: Aug. 4, 2016

(65) Prior Publication Data
US 2017/0035759 A1 Feb. 9, 2017

Related U.S. Application Data

(60) Provisional application No. 62/201,012, filed on Aug. 4, 2015.

(51) Int. Cl.
A61K 31/517 (2006.01)
A61K 31/167 (2006.01)
A61K 31/195 (2006.01)
A61K 31/42 (2006.01)
A61K 31/44 (2006.01)
A61K 31/4439 (2006.01)
A61K 31/513 (2006.01)
A61K 31/429 (2006.01)
A61K 31/437 (2006.01)
A61K 31/18 (2006.01)
A61K 31/27 (2006.01)
A61K 31/407 (2006.01)
A61K 31/506 (2006.01)

(52) U.S. Cl.
CPC .......... A61K 31/517 (2013.01); A61K 31/167 (2013.01); A61K 31/18 (2013.01); A61K 31/195 (2013.01); A61K 31/27 (2013.01); A61K 31/407 (2013.01); A61K 31/42 (2013.01); A61K 31/429 (2013.01); A61K 31/437 (2013.01); A61K 31/44 (2013.01); A61K 31/4439 (2013.01); A61K 31/506 (2013.01); A61K 31/513 (2013.01)

(58) Field of Classification Search
CPC .................................................. A61K 31/517
See application file for complete search history.

(56) References Cited

U.S. PATENT DOCUMENTS 6,068,987 A * 5/2000 Dulski ................... C12Q 1/025
435/18
8,129,418 B2 3/2012 Luesch et al.
8,217,076 B2 7/2012 Williams et al.
8,394,810 B2 3/2013 Van Duzer et al.
8,513,290 B2 8/2013 Williams et al.
2005/0277583 A1 12/2005 Yoshida et al.
2011/0060021 A1 3/2011 Cheng et al.
2013/0108655 A1 5/2013 Zabrocki et al.
2013/0224232 A1 8/2013 Zabrocki et al.
2014/0031400 A1 1/2014 Luesch et al.
2014/0093449 A1 4/2014 Williams et al.

FOREIGN PATENT DOCUMENTS

CN 101781321 A 12/2012
WO 2009126315 A2 10/2009
WO 2010009334 A1 1/2010
WO 2011113013 A2 9/2011

OTHER PUBLICATIONS

Nandarapu, D.R., et al., Design and Synthesis of Simplified Largazole Analogs as Isoform-Selective Human Lysine Deacetylase Inhibitors, Dec. 17, 2015, J Med Chem, downloaded from http://pubs.acs.org Dec. 21, 2015, 75 pages.
Archin, N.M., et al., Expression of Latent Human Immunodeficiency Typ 1 is Induced by Novel and Selective Histone Deacetylase Inhibitors, 2009, AIDS, 23:1799-1806.
Berge, S.M., et al., "Pharmaceutical Salts," 1977, J. Pharmaceutical Sciences, 66:1-19.
Bowers, A.A., et al., "Synthesis and Conformation-Activity Relationships of the Peptide Isosteres of FK228 and Largazole," 2009, J Am Chem Sci, 131/8:2900-2905.
Bowers, A.A., et al., "Synthesis and Histone Deacetylase Inhibitory Activity of Largazole Analogs: Alteration of the Zinc-Binding Domain and Macrocyclic Scaffold,"Org Ltrs, 2009, 11/6:1301-1304.
Bowers, A.A., et al., "The Total Synthesis and Biological mode of Action of Largazole: A Potent Class I Histone Deacetylase (HDAC) Inhibitor," 2008, J Am Chem Soc, 130/33:11219-11222.
Che, Y., et al., "Privileged Scaffolds Targeting Reverse-Turn and Helix Recognition," 2008, Expert Opin Ther Targets, 12/1:1-14.
Che, Y., et al., "Engineering Cyclic Tetrapeptides Containing Chimeric Amino Acids as Preferred Reverse-Turn Scaffolds," 2006, J Med Chem, 49:111-124.
Chou, C.J., et al., "Pimelic Diphenylamide 106 is a Slow, Tight-binding Inhibitor of Class I Histone Deacetylases*," 2008, J Biol Chem, 283/51:35402-35409.
Cole, K.E., "Structural Basis of the Antiproliferative Activity of Largazole, a Depsipeptide Inhibitor of the Histone Deacetylases," 2011, J Am Chem Soc, 133/32:12474-12477.
Delcuve, G.P. et al. "Roles of Histone Deacetylases in Epigenetic Regulation: Emerging Paradigms from Studies with Inhibitors," 2012, Clinical Epigenetics, 4:5, 13 pages.
Deng, K., et al, "Broad CTL Response is Required to Clear Latent HIV-1 Due to Dominance of Escape Mutations," 2015, Nature, 517, 16 pages.
Falkenberg, K.J., et al., "Histone Deacetylases and Their Inhibitors in Cancer, Neurological Diseases and Immune Disorders," 2014, Nature Reviews, Drug Discovery, 13: 673-691, 19 pages.

(Continued)

Primary Examiner — Yong S. Chong
(74) Attorney, Agent, or Firm — Stinson Leonard Street LLP

(57) ABSTRACT

Methods of using KDAC inhibitor compounds for the treatment of various parasitic diseases are described.

12 Claims, 5 Drawing Sheets

(56) References Cited

OTHER PUBLICATIONS

Falkenberg, K.J., et al., "Histone Deacetylases and Their Inhibitors in Cancer, Neurological Diseases and Immune Disorders," 2014, Nature Reviews, Drug Discovery, Supplementary Information, Table 1, 4 pages.

Falkenberg, K.J., et al., "Histone Deacetylases and Their Inhibitors in Cancer, Neurological Diseases and Immune Disorders," 2014, Nature Reviews, Drug Discovery, Supplementary Information, Tables 2A-2C, 6 pages.

Guerra-Bubb, J.M., et al., "Synthesis and HDAC Inhibitory Activity of Isosteric Thiazoline-Oxazole Largazole Analogs," 2013, Bioorg & Med Chem Ltrs, 23:6025-6028.

Hamer, D.H., "Can HIV be Cured? Mechanisms of HIB Persistence and Strategies to Combat it," 2004, Curr HIV Res, 2/2:99-11, Abstract Only, 2 pages.

Jordan, A., et al., "HIV Reproducibly Establishes a Latent Infection After Acute Infection of T Cells in vitro," 2003, The EMBO J, 22/8:1868-1877.

Keedy, K.S., et al. "A Limited Group of Class I Histone Deacetylases Acts to Repress Human Immunodeficiency Virus Type 1 Expression," 2009, J Virol, 83/10:4749-4756.

Kim, M., et al., "A Primary CD4+ T Cell Model of HIV-1 Latency Established After Activation Through the T Cell Receptor and Subsequent Return to Quiescence," 2014, Nature Protocols, 9/12:2755-2770.

Kozikowski, A.P., et al., "Use of the Nitrile Oxide Cycloaddition (NOC) Reaction for Molecular Probe Generation: A New Class of Enzyme Selective Histone Deacetylase Inhibitors (HDACIs) Showing Picomolar Activity at HDAC6," 2008, J Med Chem, 51:4370-4373.

Lassen, K.G., et al., "A Flexible Model of HIV-1 Latency Permitting Evaluation of Many Primary CD4 T-Cell Reservoirs," 2012, PLoS One, 7:1:e30176, 12 pages.

Li, X. et al., "Biologic Evaluation of New Largazole Analogues: Alteration of Macrocyclic Scaffold with Click Chemistry," 2013, ACS Med Chem Lett, 4:132-136.

Montero, A., et al., "Design, Synthesis, Biological Evaluation, and Structural Characterization of Potent Histone Deacetylase Inhibitors Based on Cyclic α/β-Tetrapeptide Architectures," 2009, J Am Chem Soc, 131/8:3033-3041.

Mwakwari, S.C., et al., "Macrocyclic Histone Deacetylase Inhibitors," 2010, Curr Top Med Chem, 10/14:1423-1440.

Olsen, C.A., et al., "Macrocyclic Peptoid-Peptide Hybrids as Inhibitors of Class I Histone Deacetylases," 2012, ACS Med Chem Lett, 3:749-753.

Rajendran, P., et al., "Metabolism as a Key to Histone Deacetylase Inhibition," 2011, Crit Rev Biochem Mol Biol, 46/3:181-199.

Reddy, D.N., et al., "Design and Synthesis of Simplified Largazole Analogues as Isoform-Selective Human Lysine Deacetylase Inhibitors," 2016, J Med Chem, 59:1613-1633.

Salvador, L.A., et al., "Discovery and Mechanism of Natural Products as Modulators of Histone Acetylation," 2012, Curr Drug Targets, 13/8:1029-1047.

Salvador, L.A., et al., "Modulation of Activity Profiles for Largazole-Based HDAC Inhibitors through Alteration of Prodrug Properties," 2014, ACS Med Chem Lett, 5/8:905-910, Abstract Only, 2 pages.

Schnekenburger, M., et al, "Epigenetic Modulators from the Big Blue: A Treasure to Fight Against Cancer," 2014, Cancer Letters, 351/2:182-197, Abstract Only, 3 pages.

Silvestri, L., et al., "Histone Deacetylase Inhibitors: Structure-Based Modeling and Isoform-Selectivity Prediction," 2012, J Chem Inf Model, A-U, 21 pages.

Taube, R., et al., "Lost in Transcription: Molecular Mechanisms that Control HIV Latency," 2013, Viruses, 5:902-928.

Valente, S., et al., "Small-Molecule Inhibitors of Histone Deacetylase for the Treatment of Cancer and Non-Cancer Diseases: A Patent Review (2011-2013);" 2014, Expert Opin Ther Patents, 24/4:401-415.

Zhang, L., et al., "Recent Progress in the Development of Histone Deacetylase Inhibitors as Anti-Cancer Agents," 2013, Mini Rev in Med Chem, 13/14:1999-2013, Abstract Only, 2 pages.

* cited by examiner

TREATMENT OF PARASITIC DISEASES USING KDAC INHIBITOR COMPOUNDS

REFERENCE TO RELATED APPLICATIONS

This application claims benefit of U.S. provisional application Ser. No. 62/201,012, filed Aug. 4, 2015, the entire disclosure of which is incorporated herein by reference.

FIELD OF THE INVENTION

The present invention generally relates to methods of using KDAC inhibitor compounds for the treatment of various parasitic diseases.

BACKGROUND OF THE INVENTION

Lysine deacetylases (KDACs), more generally referred to as histone deactylases, are a class of enzymes found in bacteria, fungi, plants, and animals that catalyze the hydrolysis of acetylated lysine side chains in histone and non-histone proteins. These enzymes are implicated in a number of biological processes such as cell differentiation, proliferation, senescence, and apoptosis. Eighteen KDACs have been identified in the human genome. Eleven human KDACs are zinc-dependent enzymes; an additional seven KDACs use nicotinamide adenine dinucleotide (NAD) as a cofactor. Zinc-dependent KDACs fall into three main classes, including class I (KDACs 1, 2, 3, and 8), class II, further subdivided into class IIa (KDACs 4, 5, 7, and 9) and class IIb (KDAC 6 and 10), and class IV (KDAC 11).

Lysine deacetylases are an epigenetic drug targets of humans, and a broad range of small-molecule inhibitors for these have been reported. In recent years, lysine deacetylases have emerged as an important class of drug targets with the potential to treat psychiatric diseases, neurodegenerative diseases, and cancer. Notwithstanding, there remains a need for new treatment methods for other diseases such as those caused by parasites.

SUMMARY OF THE INVENTION

Aspects of the present invention are directed to methods of treating various parasitic diseases using KDAC inhibitor compounds. KDAC inhibitor compounds useful in the methods of the present invention include compounds of Formulas I, II, III, IV, V, VI, VII, VIII, IX, X, or XI or a pharmaceutically acceptable salt, solvate, clathrate, prodrug, or stereoisomer thereof:

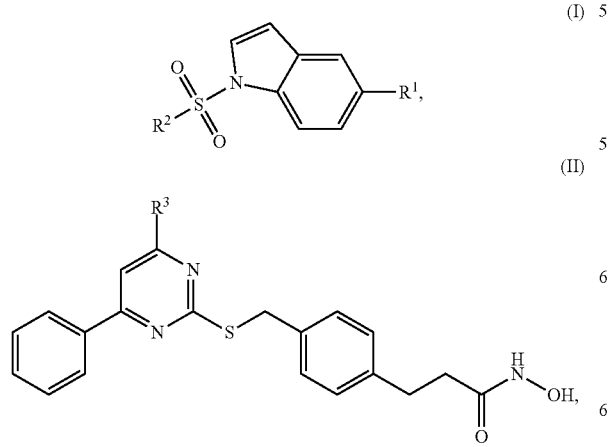

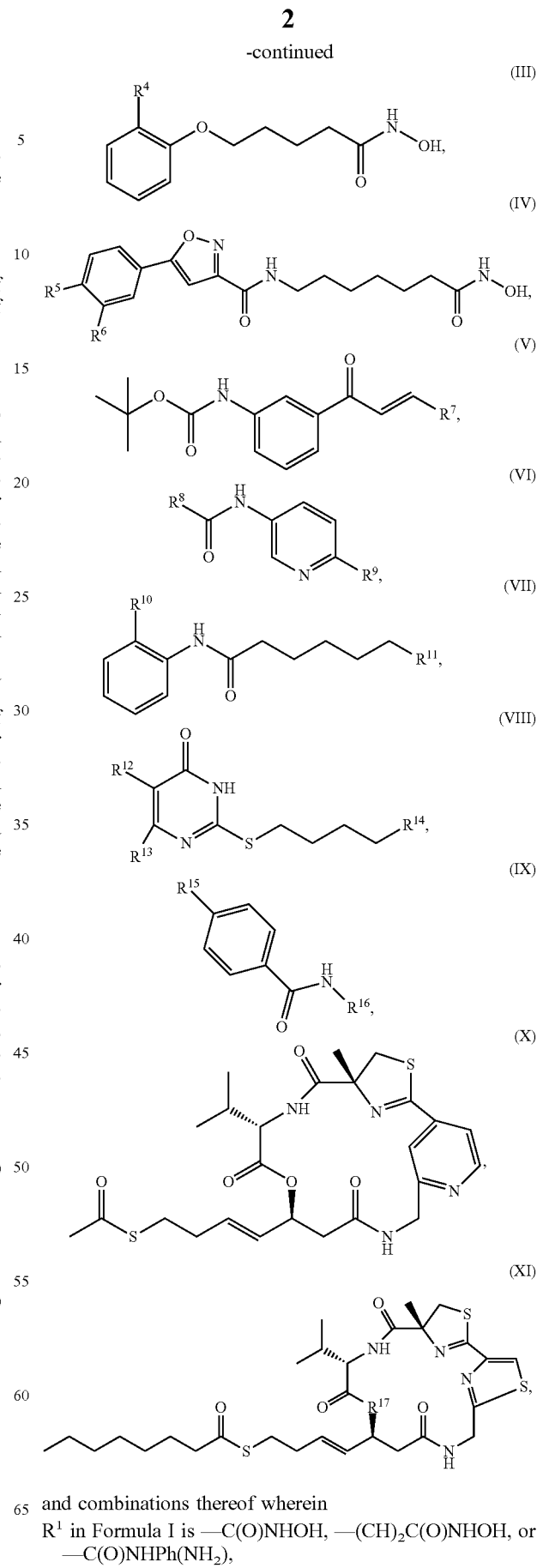

and combinations thereof wherein
$R^1$ in Formula I is —C(O)NHOH, —(CH)$_2$C(O)NHOH, or —C(O)NHPh(NH$_2$), R² in Formula I is -Ph(CH₂N(CH₃)₂), -biphenyl, or -thiophene-2-pydridine;
R³ in Formula II is halo, or —OCH₃;
R⁴ in Formula III is —C(O)OH, or —C(O)NH₂;
R⁵ and R⁶ in Formula IV are each independently hydrogen or —NHC(O)OC(CH₃)₃;
R⁷ in Formula V is -Ph((CH)₂C(O)NHOH), or —((C₄H₂N)(CH₃))C(O)NHOH;
R⁸ in Formula VI is —CH₂(C₁₀H₇), or —CH(Ph)(CH₂Ph);
R⁹ in Formula VI is —(CH)₂C(O)NHOH, or —C(O)NH((Ph)NH₂);
R¹⁰ in Formula VII is hydrogen or amine;
R¹¹ in Formula VII is —C(O)NH(Ph(CH₃)), or —CH₂C(O)NHOH;
R¹² and R¹³ in Formula VIII are each independently hydrogen, -biphenyl, or together form a fused phenyl ring;
R¹⁴ in Formula VIII is —C(O)NHOH, or —CH₂C(O)NHOH;
R¹⁵ in Formula IX is —CH₂NHC(O)OCH₂(C₅H₄N), or

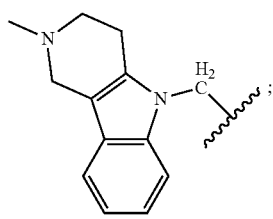 [SMILES: *Cn1c2c(c3ccccc31)CN(C)CC2]

R¹⁶ in Formula IX is —OH, or -Ph(NH₂); and
R¹⁷ in Formula XI is O or NH.

Other KDAC inhibitor compounds useful in the methods of the present invention include largazole analogs and largazole mimetics as described herein.

Further, aspects of the present invention include methods for treating a parasitic disease in a subject caused by a nematode, a protist, or a flatworm comprising administering to the subject a pharmaceutical composition comprising a therapeutically effective amount of one or more KDAC inhibitor compounds as described herein.

Other objects and features will be in part apparent and in part pointed out hereinafter.

DESCRIPTION OF THE PREFERRED EMBODIMENTS

Figure 1:
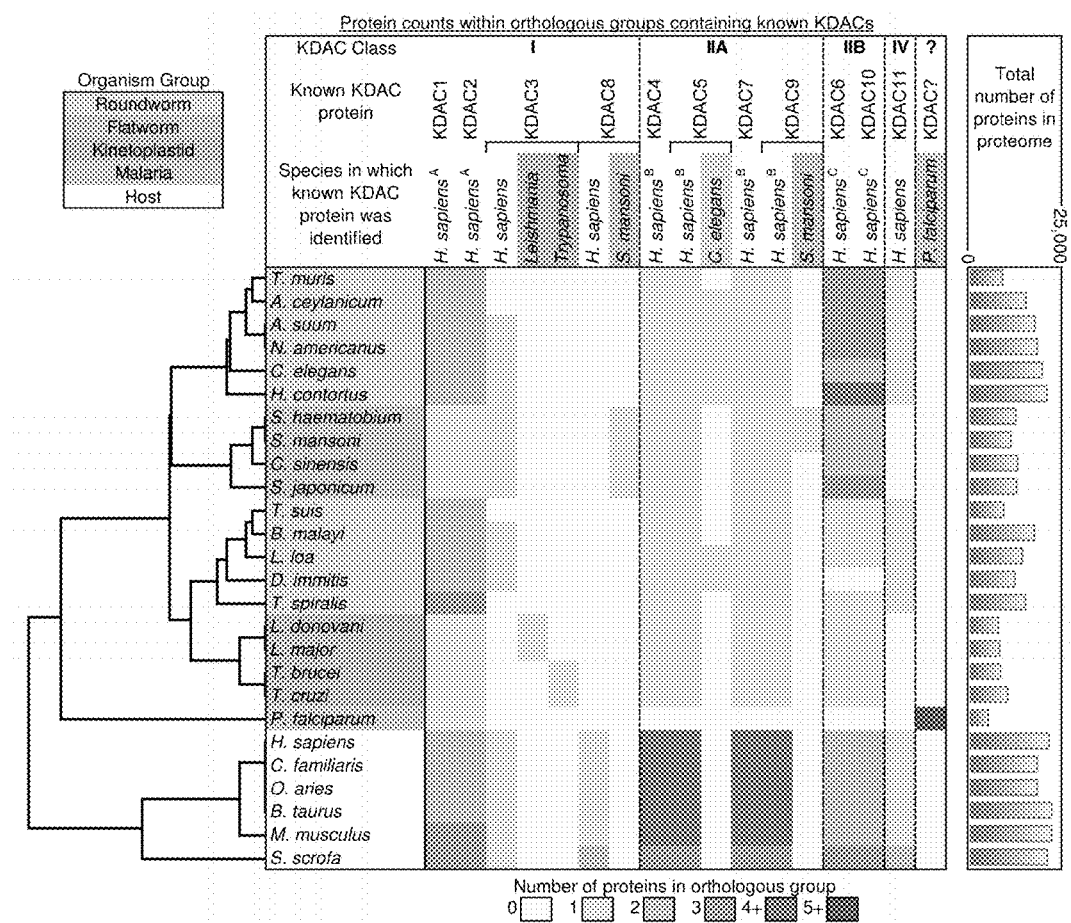
FIG. 1: KDAC proteins inferred for the parasitic species within protein families.

Generally, the present invention relates to various methods of using KDAC inhibitor compounds for treating parasitic diseases, such as malaria. In particular, the methods for treating parasitic diseases comprise administering to a subject in need thereof a pharmaceutical composition comprising a therapeutic effective amount of a KDAC inhibitor compound (i.e., a compounds that inhibits lysine deacetylase (KDAC) activity).

Parasitic diseases include those caused by a parasite selected from the group consisting of a nematode, a protist, or a flatworm. For example, the disease can be caused by parasitic nematodes such as *Brugia malayi*, *Dirofilaria immitis*, and *Haemonchus contortus* and protists such as *Trypanosoma brucei*, *Leishmania donovani*, and *Plasmodium falciparum* (pathogen of malaria).

Various KDAC inhibitor compounds useful for the methods of the present invention include compounds of Formulas I, II, III, IV, V, VI, VII, VIII, IX, X, or XI or pharmaceutically acceptable salts, solvates, clathrates, prodrugs, or stereoisomers of these compounds:

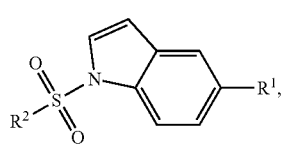

(I)

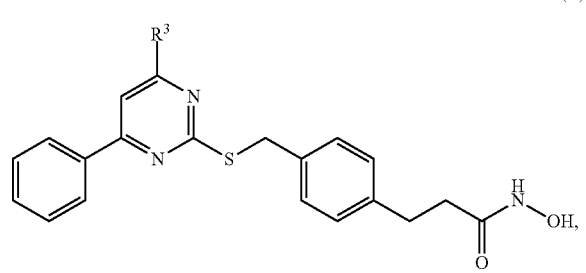

(II)

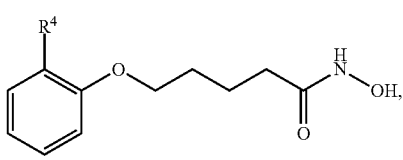

(III)

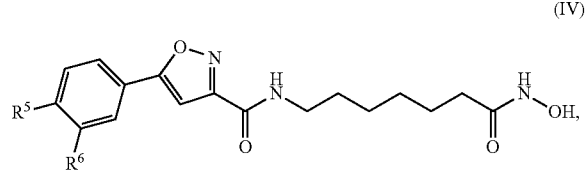

(IV)

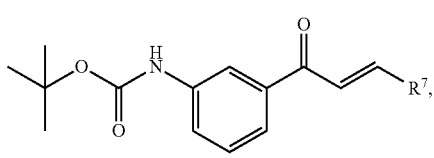

(V)

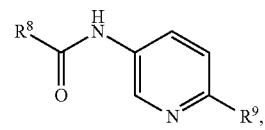

(VI)

(VII)
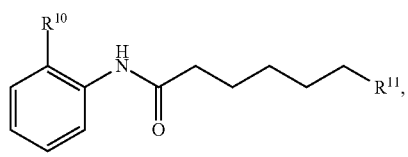

(VIII)
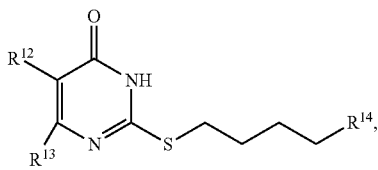

(IX)
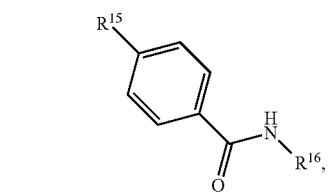

(X)
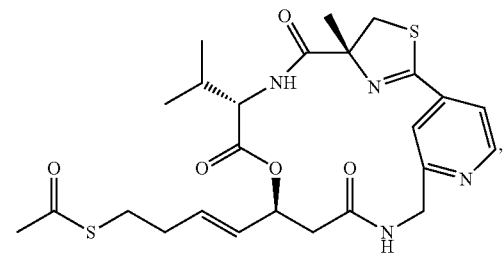

(XI)
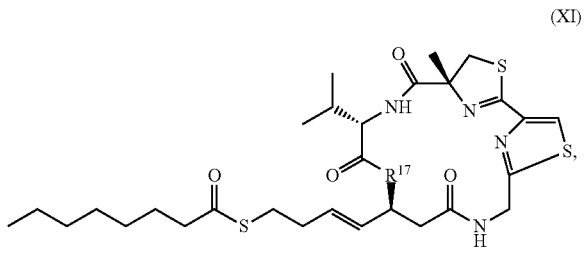

and combinations thereof wherein
$R^1$ in Formula I is —C(O)NHOH, —(CH)$_2$C(O)NHOH, or —C(O)NHPh(NH$_2$),
$R^2$ in Formula I is -Ph(CH$_2$N(CH$_3$)$_2$), -biphenyl, or -thiophene-2-pydridine;
$R^3$ in Formula II is halo, or —OCH$_3$;
$R^4$ in Formula III is —C(O)OH, or —C(O)NH$_2$;
$R^5$ and $R^6$ in Formula IV are each independently hydrogen or —NHC(O)OC(CH$_3$)$_3$;
$R^7$ in Formula V is -Ph((CH)$_2$C(O)NHOH), or —((C$_4$H$_2$N)(CH$_3$))C(O)NHOH;
$R^8$ in Formula VI is —CH$_2$(C$_{10}$H$_7$), or —CH(Ph)(CH$_2$Ph);
$R^9$ in Formula VI is —(CH)$_2$C(O)NHOH, or —C(O)NH((Ph)NH$_2$);
$R^{10}$ in Formula VII is hydrogen or amine;
$R^{11}$ in Formula VII is —C(O)NH(Ph(CH$_3$)), or —CH$_2$C(O)NHOH;
$R^{12}$ and $R^{13}$ in Formula VIII are each independently hydrogen, -biphenyl, or together form a fused phenyl ring;
$R^{14}$ in Formula VIII is —C(O)NHOH, or —CH$_2$C(O)NHOH;

$R^{15}$ in Formula IX is —CH$_2$NHC(O)OCH$_2$(C$_5$H$_4$N), or

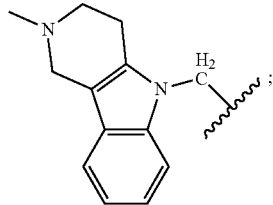 [SMILES: *Cn1c2c(c3ccccc31)CN(C)CC2]

$R^{16}$ in Formula IX is —OH, or -Ph(NH$_2$); and
$R^{17}$ in Formula XI is O or NH.

In various embodiments, the KDAC inhibitor compound of Formula I is selected from the group consisting of:

(Ia)
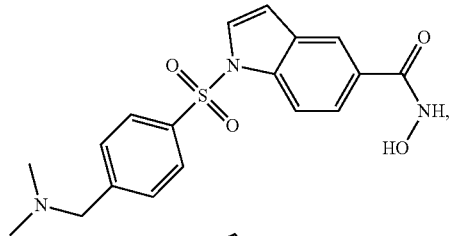

(Ib)
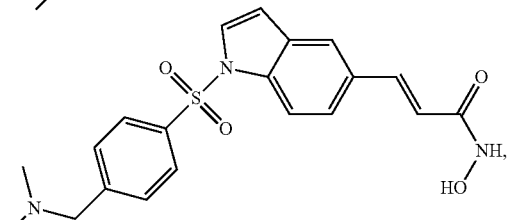

(Ic)
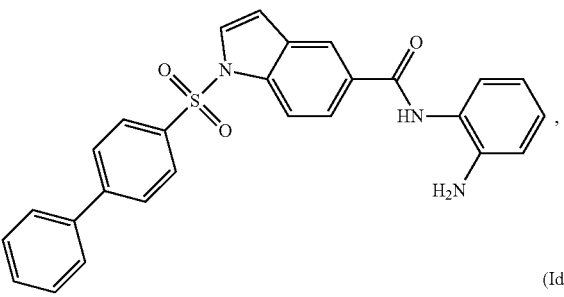

(Id)
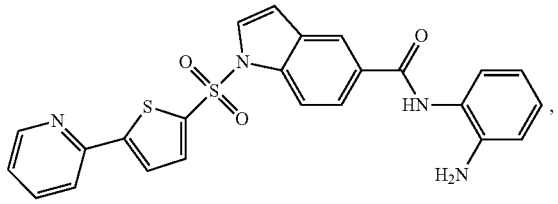

and combinations thereof.

In some embodiments, the KDAC inhibitor compound of Formula II is selected from the group consisting of:

(IIa)
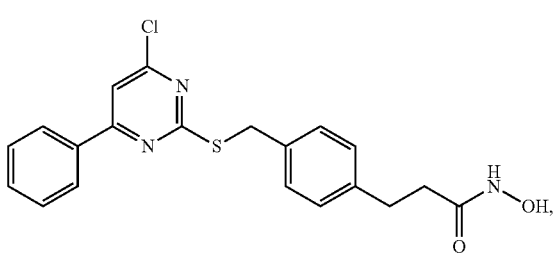

and a combination thereof.

In certain embodiments, the KDAC inhibitor compound of Formula III is selected from the group consisting of:

and a combination thereof.

In various embodiments, the KDAC inhibitor compound of Formula IV is selected from the group consisting of:

and a combination thereof.

In some embodiments, the KDAC inhibitor compound of Formula V is selected from the group consisting of:

and a combination thereof.

In certain embodiments, the KDAC inhibitor compound of Formula VI is selected from the group consisting of:

and a combination thereof.

In various embodiments, the KDAC inhibitor compound of Formula VII is selected from the group consisting of:

and a combination thereof.

In some embodiments, the KDAC inhibitor compound of Formula VIII is selected from the group consisting of:

-continued (VIIIb)

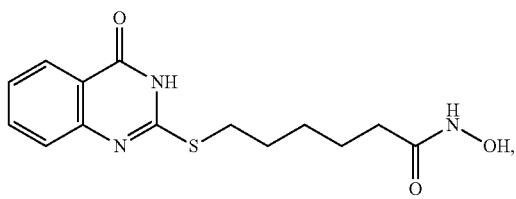

and a combination thereof.

In certain embodiments, the KDAC inhibitor compound of Formula IX is selected from the group consisting of:

(IXa)

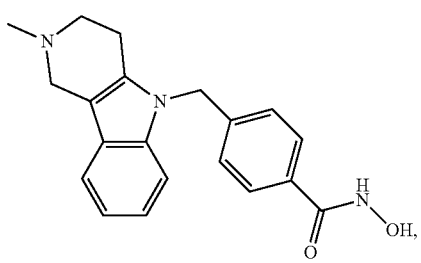

(IXb)

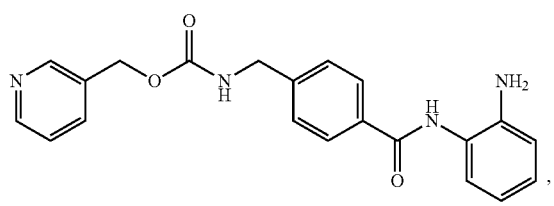

and a combination thereof.

In various embodiments, the KDAC inhibitor compound of Formula XI is selected from the group consisting of:

(XIa)

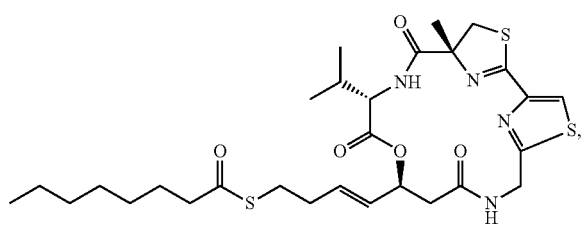

(XIb)

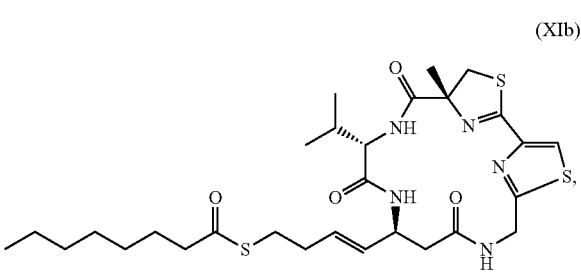

and a combination thereof.

These KDAC inhibitor compounds can be prepared using techniques known to those skilled in the art.

Other KDAC inhibitor compounds useful in the methods of the present invention include analogs of largazole (the compound of Formula XIa). Largazole analogs include, for example, peptide isosters, analogs with an oxazole-oxazoline moiety, analogs with a dithiazole moiety, analogs with a saturated side chain, analogs with a longer side chain, analogs having a valine to proline substitution, and analogs having a thiazole to pyridine substitution. One specific analog of largazole is largazole thiol, which has the following formula (XII):

(XII)

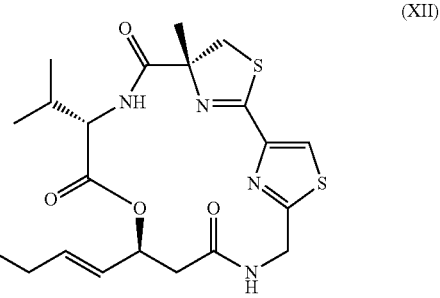

Other largazole analogs are described in U.S. Pat. No. 8,217,076, the contents of which are hereby incorporated by reference. Accordingly, in various embodiments, the largazole analog comprises a compound of Formula XIIIa or a disulfide dimer of Formula XIIIb:

(XIIIa)

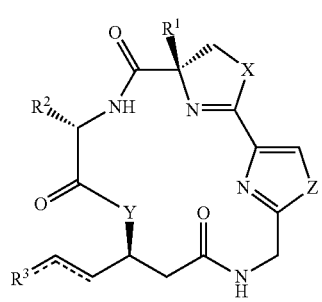

-continued

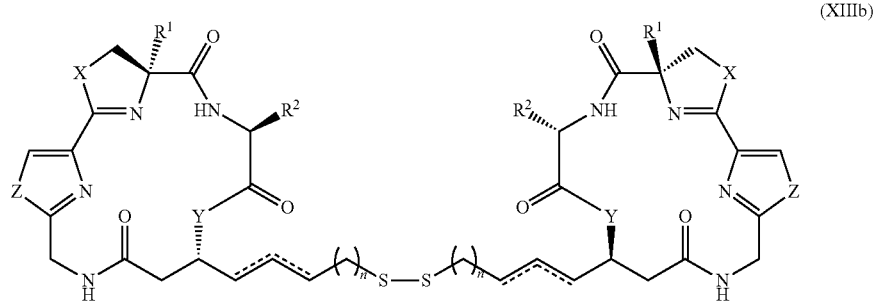
(XIIIb)

wherein in Formulas XIIIa and XIIIb:

X and Z are each independently S or O;

Y is NR or O;

R is H, lower alkyl, or lower arylalkyl;

$R^1$ is H, lower alkyl or lower arylalkyl;

$R^2$ is lower alkyl, isopropyl, n-propyl, cyclopropyl, isobutyl, n-butyl, sec-butyl, or tert-butyl;

$R^3$ is H, $(CH_2)_nCO_2H$, $(CH_2)_nCONHR$, $(CH_2)_nCONHOH$, $(CH_2)_nSR^4$, $SR^5$, $(CH_2)_nNHC(O)CH_2SR$ or

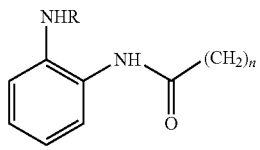

$R^4$ is H, acyl, octanoyl, a higher acyl derivative, or SR;

$R^5$ is lower alkyl or lower aryl; and n is at least 1 (e.g., 1, 2, 3, 4 or 5); or a pharmaceutically acceptable salt, solvate, clathrate, prodrug, or stereoisomer thereof.

In certain embodiments, the largazole analog comprises a compound of Formula XIIIa that is selected from the group consisting of:

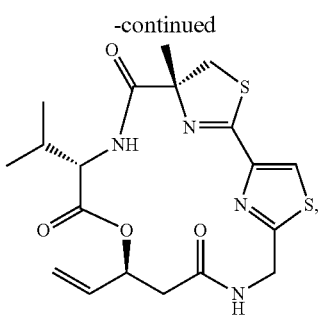

-continued

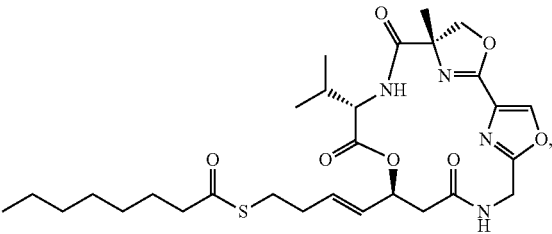

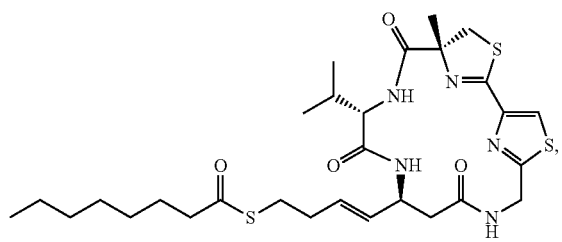

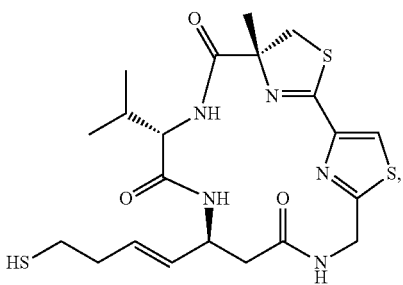

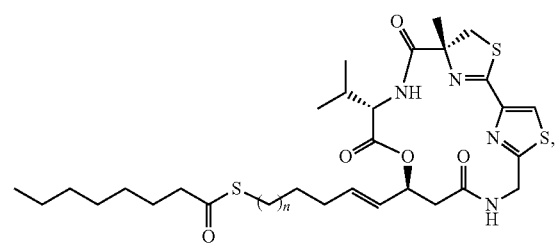

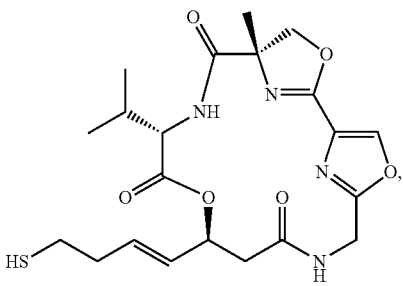

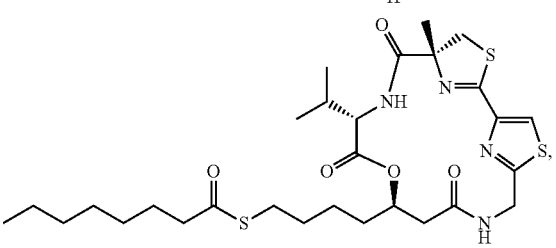

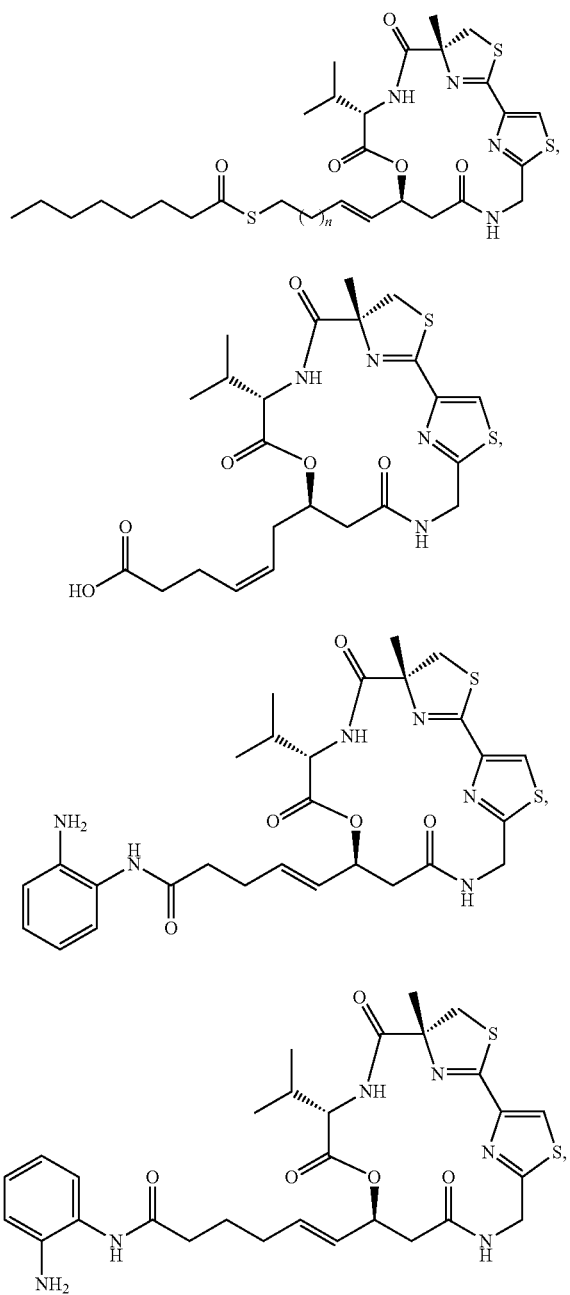
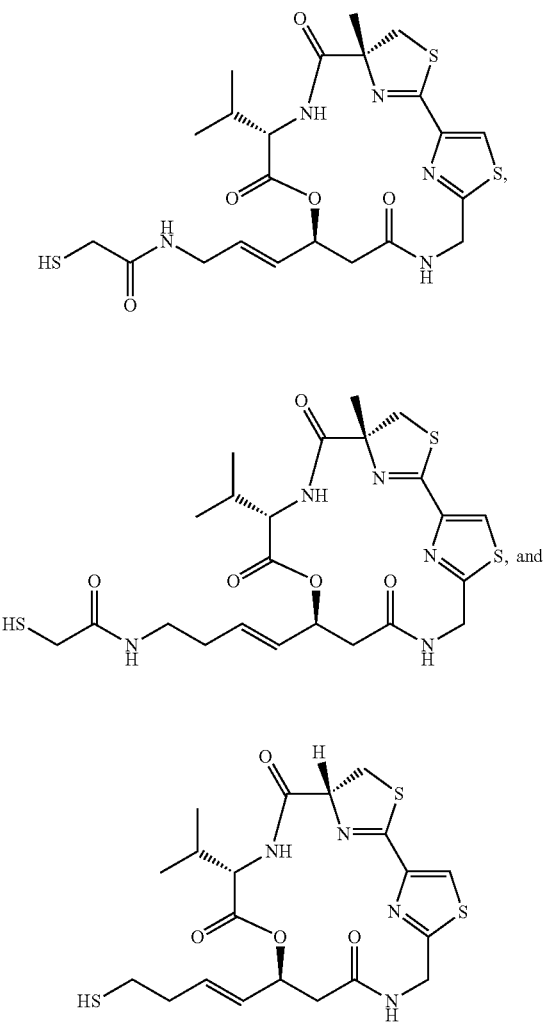
wherein n is at least 1 (e.g., 1, 2, 3, or 4).
In various embodiments, the largazole analog comprises a compound of Formula XIVa or a disulfide dimer of Formula XIVb, wherein the substituents are defined as above for compounds of Formulas XIIIa and XIIIb.
(XIVa)
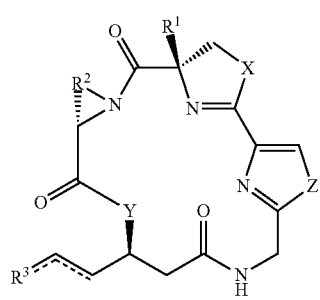

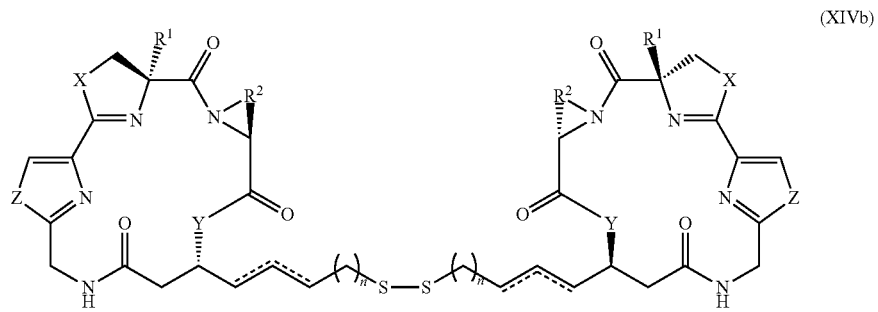
(XIVb)
An exemplary compound of Formula XIVa has the structure shown below.
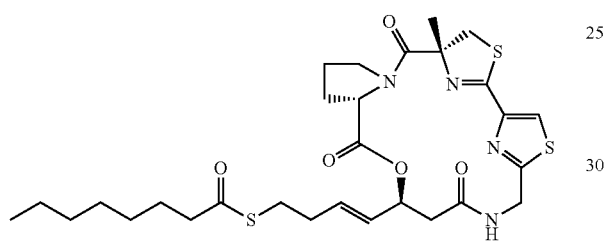
In certain embodiments, the largazole analog comprises a compound of Formula XVa or a disulfide dimer of Formula XVb wherein the substituents are defined as above for compounds of Formula XIIIa and XIIIb.
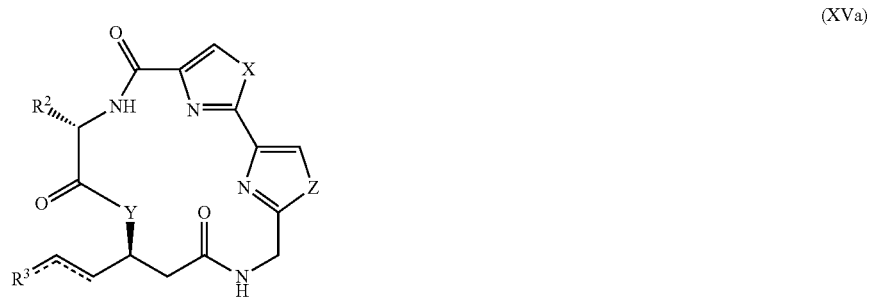
(XVa)
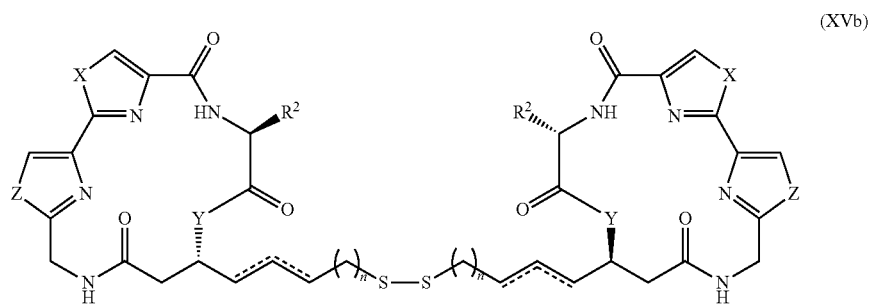
(XVb)

An exemplary compound of Formula XVa has the structure shown below.

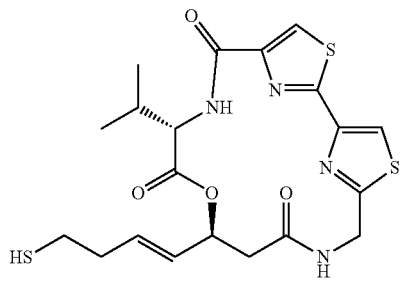 [SMILES: CC(C)[C@@H]1NC(=O)c2csc(n2)-c2csc(n2)CNC(=O)C[C@@H](/C=C/CCS)OC1=O]

In various embodiments, the largazole analog comprises a compound of Formula XVIa or a disulfide dimer of Formula XVIb:

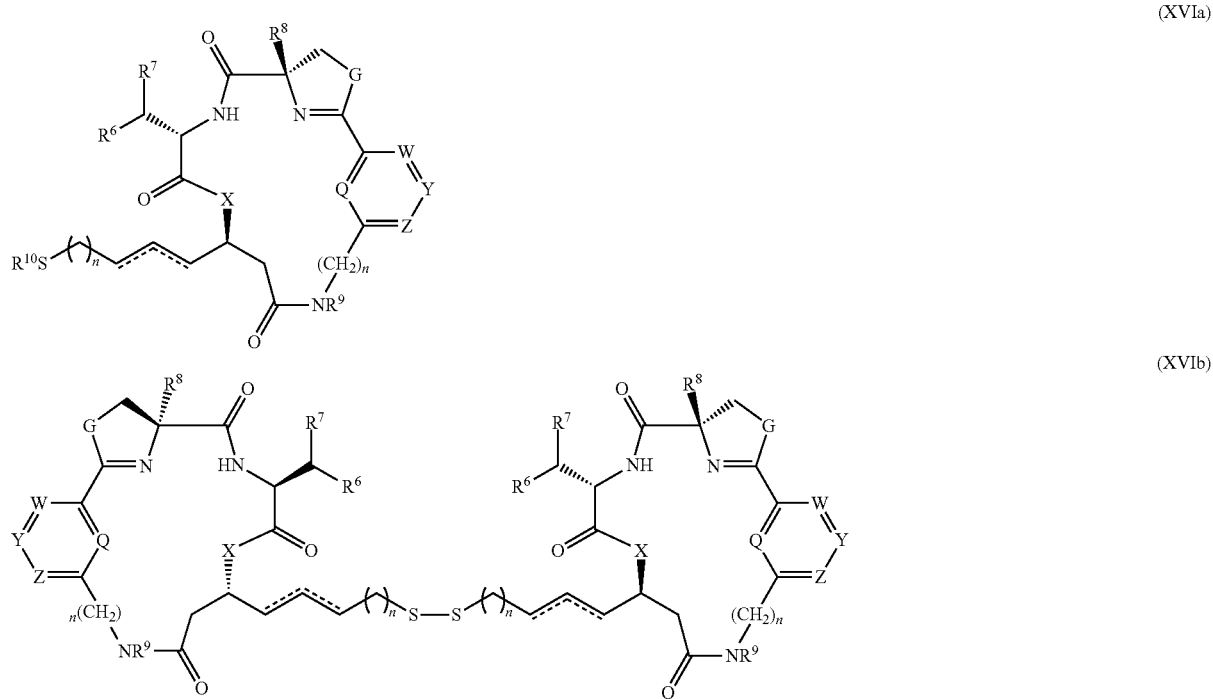

(XVIa)

(XVIb)

wherein in Formulas XVIb and XVIa:
X is O or $NR^{12}$;
G is S, O, or $NR^{12}$;
Q, W, Y, and Z are independently, N or CH, wherein at least one of Q, Y, Y, and Z is CH;
$R^6$ is and $R^7$ are each independently H or lower alkyl;
$R^8$ is H, lower alkyl, or lower arylalkyl;
$R^9$ is H or lower alkyl;
$R^{10}$ is octanoyl, $C(O)R^{11}$;
$R^{11}$ is lower alkyl, lower aryl, or lower arylalkyl;
$R^{12}$ is H lower alkyl, or lower arylalkyl; and
n is 0, 1, 2, or 3
or a pharmaceutically acceptable salt, solvate, clathrate, prodrug, or stereoisomer thereof.

Exemplary compounds of Formula XVIa include those having the following structures:

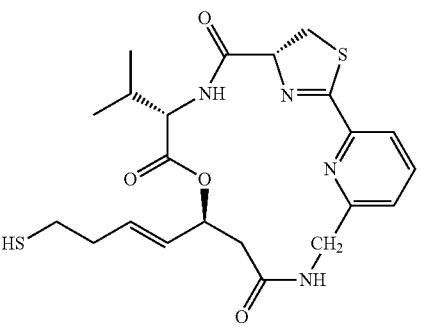

-continued

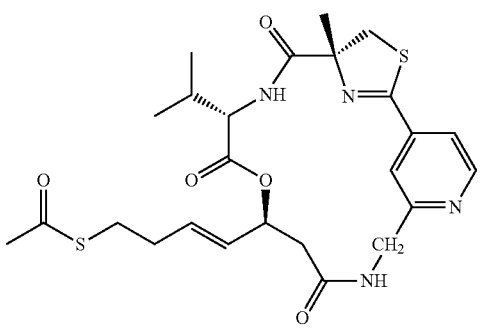

In the compounds of Formula XIII, XIV, XV, and XVI, the designation of one line parallel to a dotted line represents an optional double bond. That is, the bond can be a single bond or a double bond. When a double bond is present, the alkene may have either a cis- or trans-configuration Still other KDAC inhibitor compounds useful in the methods of the present invention include largazole mimetics such as those described in International Application No. PCT/US2016/030995, which is incorporated herein by reference. These largazole mimetics are compounds of general Formula XVII:

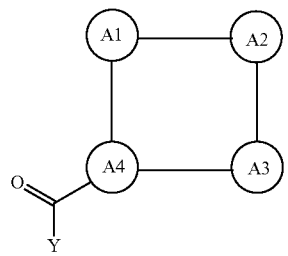

(XVII)

wherein A1 and A2 are each independently L-Pro, D-Pro, L-NMe-AA or D-NMe-AA; A3 is a natural or unnatural alpha-amino acid; and A4 is L- or D-aspartic wherein the α-carboxyl group is unprotected (Y═OH) or wherein the α-carboxyl group has been converted to an ester or amide derivative.

Preferably, the largazole mimetics include compounds of Formula XVIIa, XVIIb, XVIIc, and/or XVIId or a pharmaceutically acceptable salt, solvate, prodrug, or stereoisomer thereof, having a diproline subunit at A1-A2, a naturally occurring L-amino acid at A3, and L- or D-aspartic acid (or ester or amide derivative thereof) at A4 as shown below:

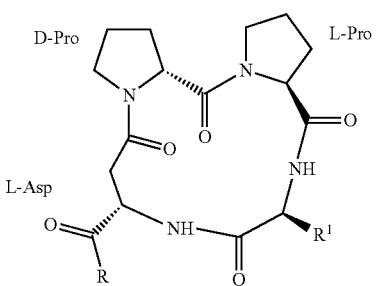

(XVIIa)

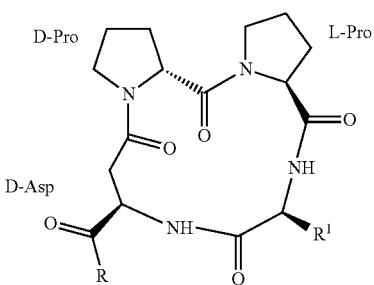

(XVIIb)

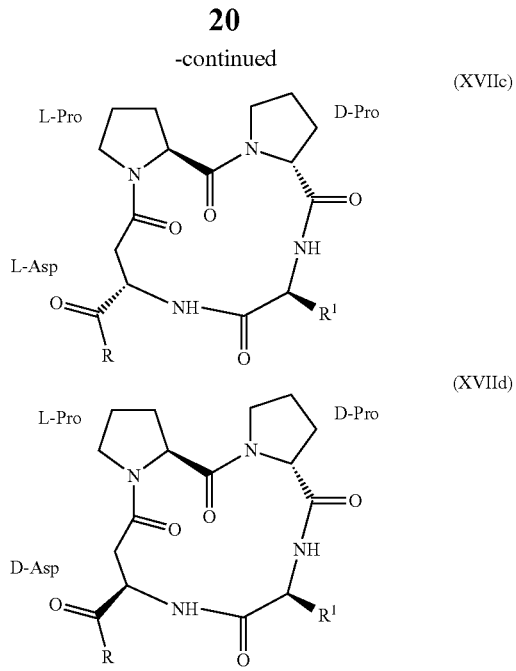

(XVIIc)

(XVIId)

wherein in Formulas XVIIa, XVIIb, XVIIc, and XVIId:
R is hydroxyl, substituted or unsubstituted alkoxy, substituted or unsubstituted aryloxy, substituted or unsubstituted arylalkyloxy, or substituted or unsubstituted amino; and $R^1$ is a naturally occurring L-amino acid.

Compounds of Formulas XVIIa, XVIIb, XVIIc, and XVIId are cyclic tetrapeptides having a 13-membered ring derived from three alpha-amino acids and one beta-amino acid (i.e., α3β architecture). Compounds of Formula XVIIa and XVIIb have the dipeptide subunit D-Pro-L-Pro, whereas compounds of Formula XVIIc and XVIId have the dipeptide subunit L-Pro-D-Pro. The third amino acid is a naturally occurring L-amino acid, and the fourth amino acid is a β-amino acid which is L-Asp (compounds XVIIa and XVIIc) or D-Asp (compounds XVIIb and XVIId).

The $R^1$ group in these compounds derives from the third amino acid. In various embodiments, $R^1$ is H (Gly), Me (Ala), isopropyl (Val), isobutyl (Leu), or sec-butyl (Ile). Side chains from other natural amino acids are also included. In preferred embodiments, $R^1$ is isopropyl (Val).

The cyclic tetrapeptide also has a side chain that is a carboxyl group, corresponding to the α-carboxyl group of L- or D-aspartic acid, or a derivative thereof. The carboxyl group can be converted, for example, into an ester. Accordingly, in Formulas XVIIa, XVIIb, XVIIc, and XVIId, R can be hydroxy, substituted or unsubstituted alkoxy, substituted or unsubstituted aryloxy, or substituted or unsubstituted arylalkyloxy. In various embodiments, R is hydroxy, substituted or unsubstituted $C_1$-$C_6$ alkoxy, substituted or unsubstituted phenoxy, or substituted or unsubstituted benzyloxy. In certain embodiments, R is hydroxy or benzyloxy.

The carboxyl group can also be converted into an amide. Accordingly, in Formulas XVIIa, XVIIb, XVIIc, and XVIId, R can be amino ($NH_2$) or substituted amino. In various embodiments, R is substituted amino having the formula —NH—(CH)$_n$—$R^2$, where $R^2$ is OH, $SR^3$, $SOR^3$, $SO_2R^3$, $NR^3$, $CO_2R^3$, $C(O)NHOR^3$, S—S(CH$_2$)—NH$_2$, —NH(CH$_2$)$_n$S—S(CH$_2$)$_n$NHPO(OR$^4$)$_2$; $R^3$ is hydrogen or $C_1$-$C_6$ alkyl (e.g., methyl or ethyl); $R^4$ is hydrogen or phenyl; and n is a number from 2 to 5 (e.g., n can be 2 to 3).

As used herein, "lower alkyl" or "lower alkyl moieties" contain from 1-12 carbon atoms, "lower aryl" or "lower aryl moieties" contain from 6-12 carbon atoms, and "lower arylalkyl" or "lower arylalkyl moieties" contain from 7-12 carbon atoms. In a preferred embodiment, lower alkyl refers to a $C_{1-7}$ alkyl, lower aryl refers to a $C_{6-10}$ aryl, and lower arylalkyl refers to a $C_{7-11}$ aralkyl. Included are substituted derivatives of lower chain alkyl, aryl and arylalkyl moieties, wherein the substituent is selected from (but are not limited to) one or more of the following chemical moieties: —OH, —OR, —COOH, —COOR, —CONH$_2$, —NH$_2$, —NHR, —NRR, —SH, —SR, —SO$_2$R, —SO$_2$H, —SOR, —PO$_3$R, —OPO$_3$R, and halogen (including F, Cl, Br and I), wherein each occurrence of R is independently selected from a lower chain alkyl, aryl or arylalkyl moiety. Moreover, cyclic lower chain alkyl, aryl and arylalkyl moieties of the invention include naphthalene, as well as heterocyclic compounds such as thiophene, pyrrole, furan, imidazole, oxazole, thiazole, pyrazole, 3-pyrroline, pyrrolidine, pyridine, pyrimidine, purine, quinoline, isoquinoline and carbazole.

In various embodiments, the KDAC inhibitor compound can be selective for inhibiting the lysine deacetylase activity of at least one isoform selected from the group consisting of KDAC1, KDAC2, KDAC3, KDAC4, KDAC5, KDAC6, KDAC7, KDAC8, KDAC9, KDAC10, KDAC11, and a combination thereof. For example, the KDAC inhibitor can be selective for inhibiting the lysine deacetylase activity of at least one KDAC isoform with an inhibiting activity (IC$_{50}$) from about 10 to about 0.02 nanomolar. In various embodiments, the KDAC inhibitor is selective toward at least one of KDAC1, KDAC2, KDAC3, and KDAC8.

In accordance with other aspects of the present invention, the compounds of the present invention can be formulated in a suitable pharmaceutical composition. Generally, the pharmaceutical composition comprises a therapeutically effect amount of at least one KDAC inhibitor (e.g., a compound of Formula I, II, III, IV, V, VI, VII, VIII, IX, X, XI, a largazole analog, a largazole mimetic, or a combination thereof) and one or more excipients.

Pharmaceutical compositions containing the compounds of the present invention can be formulated in any conventional manner. Proper formulation is dependent in part upon the route of administration selected. Routes of administration include, but are not limited to, oral, parenteral (e.g., intravenous, intra-arterial, subcutaneous, rectal, subcutaneous, intramuscular, intraorbital, intracapsular, intraspinal, intraperitoneal, or intrasternal), topical (nasal, transdermal, intraocular), intravesical, intrathecal, enteral, pulmonary, intralymphatic, intracavital, vaginal, transurethral, intradermal, aural, intramammary, buccal, orthotopic, intratracheal, intralesional, percutaneous, endoscopical, transmucosal, sublingual and intestinal administration.

Pharmaceutically acceptable excipients for use in the compositions of the present invention are selected based upon a number of factors including the particular compound used, and its concentration, stability and intended bioavailability; the disease, disorder or condition being treated with the composition; the subject, its age, size and general condition; and the route of administration.

The pharmaceutical compositions can be formulated, for example, for oral administration. The pharmaceutical compositions can be formulated as tablets, dispersible powders, pills, capsules, gel-caps, granules, solutions, suspensions, emulsions, syrups, elixirs, troches, lozenges, or any other dosage form that can be administered orally. Pharmaceutical compositions for oral administration can include one or more pharmaceutically acceptable excipients. Suitable excipients for solid dosage forms include sugars, starches, and other conventional substances including lactose, talc, sucrose, gelatin, carboxymethylcellulose, agar, mannitol, sorbitol, calcium phosphate, calcium carbonate, sodium carbonate, kaolin, alginic acid, acacia, corn starch, potato starch, sodium saccharin, magnesium carbonate, microcrystalline cellulose, colloidal silicon dioxide, croscarmellose sodium, talc, magnesium stearate, and stearic acid. Further, such solid dosage forms can be uncoated or can be coated to delay disintegration and absorption.

In another aspect, the pharmaceutical compositions can be formulated for parenteral administration, e.g., formulated for injection via intravenous, intra-arterial, subcutaneous, rectal, subcutaneous, intramuscular, intraorbital, intracapsular, intraspinal, intraperitoneal, or intrasternal routes. Dosage forms suitable for parenteral administration include solutions, suspensions, dispersions, emulsions or any other dosage form that can be administered parenterally.

Pharmaceutically acceptable excipients are identified, for example, in *The Handbook of Pharmaceutical Excipients*, (American Pharmaceutical Association, Washington, D.C., and The Pharmaceutical Society of Great Britain, London, England, 1968). Additional excipients can be included in the pharmaceutical compositions of the invention for a variety of purposes. These excipients can impart properties which enhance retention of the compound at the site of administration, protect the stability of the composition, control the pH, facilitate processing of the compound into pharmaceutical compositions, and so on. Other excipients include, for example, fillers or diluents, surface active, wetting or emulsifying agents, preservatives, agents for adjusting pH or buffering agents, thickeners, colorants, dyes, flow aids, non-volatile silicones, adhesives, bulking agents, flavorings, sweeteners, adsorbents, binders, disintegrating agents, lubricants, coating agents, and antioxidants.

As used herein, the term "therapeutically effective amounts" of a therapeutic agent can be determined in many different ways, such as assaying for an improvement of physiological condition of a subject. Effective amounts also can be determined through various in vitro, in vivo or in situ assays.

"Pharmaceutically acceptable salt" as used herein refers to salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). Examples of pharmaceutically acceptable include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "prodrug" refers to a derivative of a compound that can hydrolyze, oxidize, or otherwise react under biological conditions (in vitro or in vivo) to provide a compound of the invention. Prodrugs may only become active upon some reaction under biological conditions, but they may have activity in their unreacted forms. Examples of prodrugs contemplated herein include, without limitation, analogs or derivatives of compounds of the invention. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Prodrugs and their uses are well known in the art (see, e.g., Berge, et al. 1977 J. Pharm. Sci. 66:1-19). Prodrugs can typically be prepared using well-known methods, such as those described in Burger's Medicinal Chemistry and Drug Discovery (1995, Manfred E. Wolff ed., 5thed. 172-178, 931-932).

It will be noted that the structure of some of the compounds of this invention includes asymmetric carbon atoms, and thus may exist as racemic mixtures or as isolated isomeric forms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis. Furthermore, the structures and other compounds and moieties discussed in this application also include all tautomers thereof.

"Subject" as used herein refers to a mammal, including both human and non-human mammals. Subjects include veterinary subjects, including livestock such as cows and sheep, rodents (such as mice and rats), and non-human primates. Preferred subjects are mammals and human subjects.

"Treat", "treating", and "treatment" refer to a method of alleviating or abating a disease and/or its attendant symptoms.

Having described the invention in detail, it will be apparent that modifications and variations are possible without departing from the scope of the invention defined in the appended claims.

EXAMPLES

The following non-limiting examples are provided to further illustrate the present invention.

Example 1

Data Collection

Whole proteome data from 26 eukaryotic species were collected. The datasets were comprised of 11 species of nematodes, 4 species of platyhelminthes, 5 species of protists (kinetoplastids and pathogen of malaria) and 6 species of hosts/outgroups. Data were downloaded as follows: for the outgroups, Homo sapiens and Mus musculus were from Ensembl release 67; and Bos taurus, Canis lupus familiaris, Sus scrofa and Ovis aries were from Genbank release 102, 102, 103, and 100 respectively. For the nematodes, Caenorhabditis elegans and Brugia malayi were from Wormbase WS230; Trichinella spiralis, Dirofilaria immitis, Ascaris suum, Haemonchus contortus, and Necator americanus were from published data. Trichuris muris was from the Sanger Institute release (<ftp://ftp.sanger.ac.uk/pub/pathogens/Trichuris/muris/>). Loa loa was from Broad Institute release (<http://www.broadinstitute.org>). The other 2 nematode species, Ancylostoma ceylanicum and Trichuris suis were from our in-house sequencing datasets. For the platyhelminthes, Schistosoma japonicum was from Chinese National Human Genome Center at Shanghai (<http://lifecenter.sgst.cn/schistosoma/en/schistosomaCnIndexPage.do#Download>); Schistosoma mansoni was from the Sanger Institute release (<ftp://ftp.sanger.ac.uk/pub/pathogens/Schistosoma/mansoni/genome/gene_predictions/GeneDB_Smansoni_Proteins. v4.0g.gz>, retrieved on Feb. 29, 2009); Schistosoma haematobium was downloaded from SchistoDB (<http://SchistoDB.net>) on Feb. 1, 2012; and Clonorchis sinensis was downloaded from NCBI (NCBI bioproject 72781). All the kinetoplastids (Trypanosoma brucei, Trypanosoma cruzi, Leishmania major, and Leishmania donovani) were downloaded from TriTrypDB (<http://tritrypdb.org>) on Jan. 7, 2014 (release 6.0). Plasmodium falciparum was downloaded from NCBI (<ftp://ftp.ncbi.nih.gov/genomes/Protozoa/Plasmodium_falciparum/>) on Jan. 7, 2014. Isoforms of these downloaded sequences were examined against the coding genes, and only the longest ones were kept when applicable.

Example 2

Protein Family Definition and Identification of KDAC Protein Families

Protein families (orthologous groups) were defined utilizing the Markov cluster algorithm of the OrthoMCL package with an inflation factor 1.5 based on the proteomes. Each protein family consists of at least two proteins from one or more species. The gene annotations of KDAC proteins for human in Ensembl, as well as those reported in literature for the pathogens malaria, toxoplasmosis, trypanosomiasis, schistosomiasis, and leishmaniasis were used to identify and manually curate the KDAC protein families. The number of proteins in each of these protein families was used to cluster the 26 species, using Manhattan clustering with average linkage using the software package GENE-E (<http://www.broadinstitute.org/cancer/software/GENE-E/>). A heatmap based on orthologous protein data is shown in FIG. 1.

Example 3

Screening in Parasitic Species and Mammalian Cell Line

Figure 5:
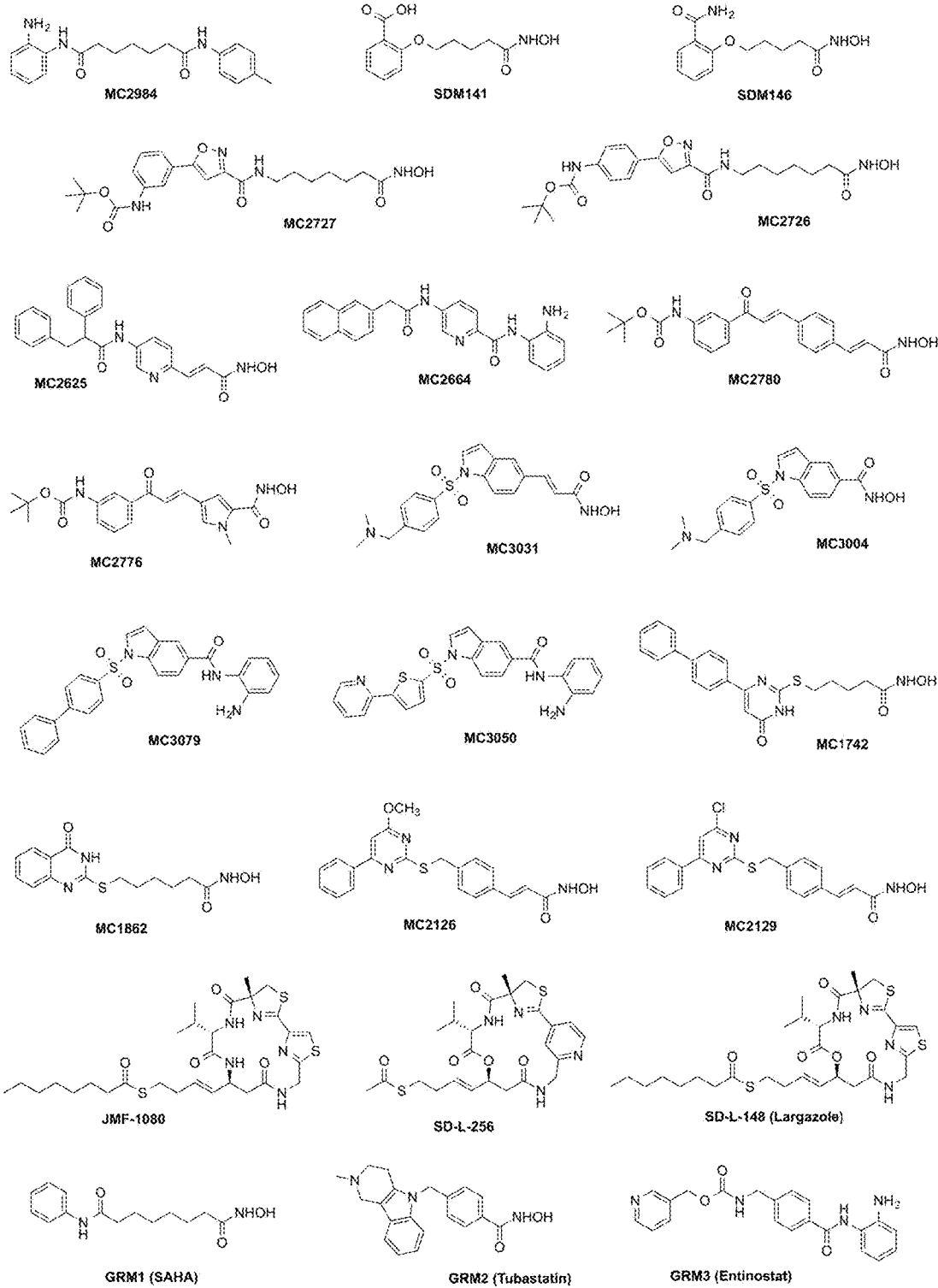
FIG. 5: Structures of the compounds tested for antiparasitic activity in Example 3.

Compounds were selected based on the following criteria: 1) known KDAC inhibitors which have been well studied and characterized in human study, usually used as controls, e.g. GRM1 (SAHA), GRM2 (Tubastatin), and GRM3(Entinostat); 2) cyclic depsipeptide based, class I-selective KDAC inhibitors and their analogs, e.g. SD-L-148 (Largazole), SD-L-256, JMF-1080; 3) other hydroxamate- or benzamide-based small molecules which have been shown to be human KDAC inhibitors in purified enzyme-based assays. The structures of the compounds are shown in FIG. 5.

The selected compounds were tested against three parasite groups (two nematodes and three protists) and a mammalian cell line (L929 mouse fibroblast; NCTC clone 929 [L cell, L-929, derivative of Strain L] was obtained from ATCC), Table 1.

automated liquid-handling equipment. Test compounds in DMSO were added to each well at 2-5 μM for $T.$ $brucei$ and 5-10 μM for $L.$ $donovani$ followed by incubation with the parasite for 72 hours at 37° C. with 5% $CO_2$. Known anti-trypanosomal compounds, i.e. pentamidine and suramin, were included in each plate to serve as positive controls. Parasite viability was determined by the addition of resazurin and plates were evaluated using a fluorescent plate reader. Compounds showing ≥75% inhibition in primary assays were selected and titrated to confirm their activity and to generate $IC_{50}$ values. Activity/base protocols were used to calculate $IC_{50}$ values and generate quality control parameters for each plate and are listed in Table 1.

TABLE 1

Compound screening in host cells and parasites.

| | Assay | | | | | | |
|---|---|---|---|---|---|---|---|
| | CYT vt | Endoparasites_DR | | | HAT vt | LEI axe | MAL vt |
| | | Cell In/species | | | | | |
| | L929 | B. malayi | D. immitis | H. contortus | TBBS427 | Ld1S | PfDd2 |
| | | Time point | | | | | |
| Compound | 5 day | 72 hour | 96 hour | $IC_{50}$ (nM) | 72 hour | 72 hour | 15 minute |
| MC2984 | | | | | | | |
| MC3031 | 0.555 | | | | 0.267 | >5 | |
| SDM141 | | | | | | | |
| SDM146 | | | | | | | |
| MC2664 | | | | | | | |
| MC2126 | 1.76 | | | | 0.441 | >5 | 1.92 |
| MC3004 | | | | | | | |
| MC3079 | | | | | | | |
| MC2726 | 1.92 | | | | | | 0.189 |
| MC2727 | 2.35 | | | | | | 0.96 |
| MC2780 | 4.81 | 2.53 | 8.14 | | 0.623 | 0.473 | 0.056 |
| MC2776 | >10 | 4.39 | >10 | | | | |
| MC3050 | | | | | | | |
| MC2625 | 0.311 | | | | 1.18 | >5 | 0.022 |
| MC2129 | | | | | | | |
| GRM1 | 0.155 | | | | 1.81 | >5 | 0.152 |
| MC1742 | 1.51 | | | | | | <0.01 |
| MC1862 | 7.12 | | | | | | 1.15 |
| GRM2 | 6.22 | | | | 2.7 | >5 | |
| GRM3 | | | | | | | |
| SD-L-256 | 0.333 | >10 | >10 | 0.9 | | | |
| SD-L-148 | 0.101 | | | 7.1 | | | |
| JMF-1080 | | | | | | | |

Compound screening against nematodes was conducted using three organisms with very different modes of parasitism: the blood feeding and gut dwelling $H.$ $contortus$, and the animal and human tissue-dwelling filarial nematodes $D.$ $immitis$ and $B.$ $malayi$.

Cytotoxicity viability assays (CYT vt) using L929 mouse fibroflasts (L929), endoparasites dose response assay (endoparasites DR) using $B.$ $malayi$, $D.$ $immitis$, and $H.$ $contortus$, Human Afrian trypanosome viability assay (HAT vt) using $T.$ $brucei$ strain S427 (Tbb S427), $Leishmania$ axenic amastigote assay (LEI axe) using $L.$ $donovani$ strain MHOM/SD/00/LS (Ld1S), and malaria viability assay (MAL vt) using $P.$ $falciparum$ 3D7 strain (PfDd2) were performed using the compounds disclosed herein (Table 1).

The kinetoplastids viability assays were conducted with exponentially growing trypomastigotes, oraxenic amastigotes, for each species respectively in 96-well plates using Compounds with $IC_{50}$≤1 μM for $T.$ $brucei$ and $IC_{50}$<5 μM for $L.$ $donovani$ were tested versus mammalian cells to determine parasite versus host-cell selectivity. A $P.$ $falciparum$ viability assay was conducted with the 3D7 strain of $P.$ $falciparum$ known to be sensitive to all antimalarial drugs. Assays were performed in 96-well microtiter plates and each well contained 100 μl of parasite culture maintained in media supplemented with human red blood cells (0.5% parasitemia, 2.5% hematocrit) in a humidified atmosphere at 37° C., 5% $O_2$, and 5% $CO_2$.

Test compounds in DMSO were added to each well at a concentration of approximately 2-5 μM. After incubation, 85% of the supernatant was removed and cells were washed with PBS. A DNA-specific dye (SYBR Green or DAPI) was added in the presence of lysis agents, saponin and Triton X-100. Plates were incubated for 15 min and then read in a fluorescent microplate reader. Compounds showing ≥75% inhibition in primary assays were cherry-picked and titrated to confirm activity and generate $IC_{50}$ values. Activity/Base protocols were used to calculate $IC_{50}$ values and generate quality control parameters for each plate. Compounds with $IC_{50} \leq 1$ µM were tested against mammalian cells (to determine parasite versus host-cell selectivity) and also against a selection of drug-resistant strains of *P. falciparum*.

A total of 13 compounds out of the 23 screened showed efficacy in at least one parasite, with all of them also showing some kind of activity on the mammalian cell lines (Table 1). Most of the active compounds showed extremely high (nM to sub-nM $IC_{50}$) potency in the inhibition of *P. falciparum* growth. Approximately 10 compounds had an $IC_{50}/EC_{50}$ lower (ratio <0.5) in at least one parasite species compared to the host-cell line. One of the compounds (MC2776), a pyrrole-based hydroxyamate derivative, showed considerable potency ($EC_{50}$=4.39 µM) on the nematode *B. malayi*, without detectable activity in the host-cell line (>10 µM), making it a candidate for further optimization and in-depth study. The activity of compound MC2776 was higher than 10 µM $IC_{50}$ on human cancer cell lines and had a more potent $IC_{50}$ than compound MC2780. None of the benzamide analogs showed activities on these cell lines (>20 µM). Without being bound by theory, it is believed that there is a possible role for the hydroxmate/benzamide group on cell permeability/transport.

Example 4

Protein Structural Modeling and Ligand Docking

For those KDAC isotypes in parasitic species targeted by active compounds, homology models were built by using the X-ray structure of the human ortholog as a template, using the ROSETTA3.4 macromolecular modeling package. The catalytic zinc ion at the active site was modeled explicitly to mimic the square-based pyramidal geometry as observed in crystal structures. After the initial comparative modeling and loop building, each protein model was relaxed with the following constraints to achieve the desired geometry: the zinc ion was constrained to have the axial position coordinated to the conserved histidine residue (HIS, deprotonated NO, two equatorial positions coordinated to the conserved aspartic acid residues (ASP, deprotonated hydroxyl oxygen) and the remaining two equatorial positions coordinated to solvent water molecules. One hundred models for each target were generated using the constrained relaxation procedure, and the one with the lowest total energy was chosen as the final protein model for subsequent docking studies. For each small ligand to be docked, OMEGA was used to generate a conformer library; OpenEye's AM1-BCC implementation was used to calculate partial charges. The hydroxamate group was deprotonated in the modeling process, as suggested by previous docking and virtual screening reports. The ligands were docked to the models in ROSETTA using the ligand_dock application by specifying a constraint of the hydroxamate group to be coordinated to the zinc, replacing the two water molecules used in modeling the zinc geometry. One hundred poses were generated for each compound at each target, the 5 best-scoring poses were selected for manual inspection, and a representative pose was finally chosen for interpretation.

Figure 2:
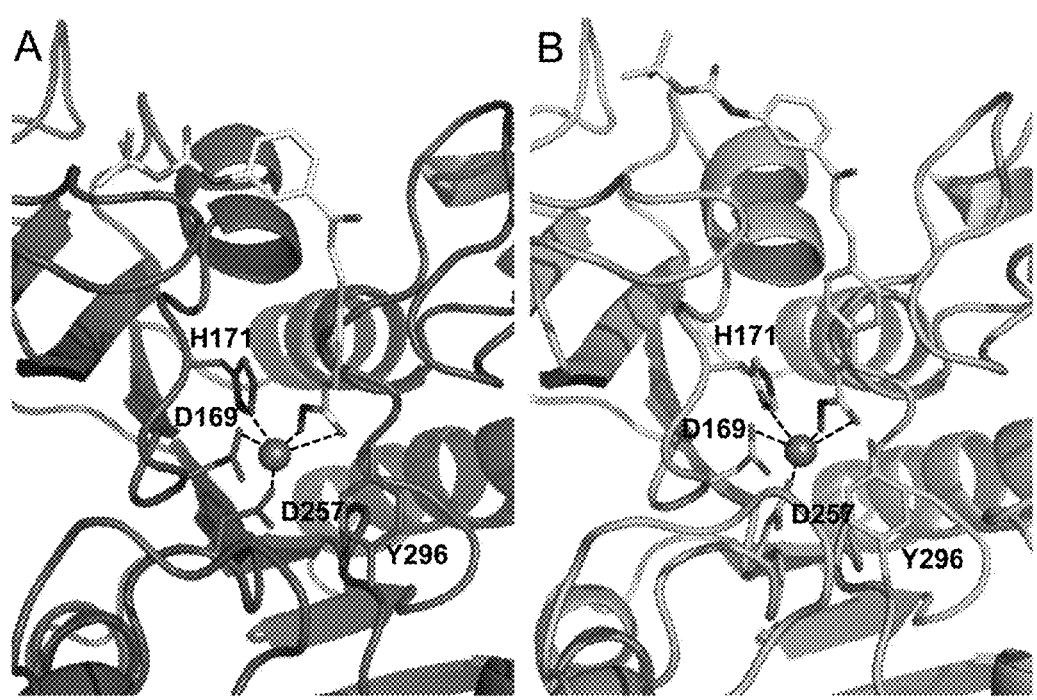
FIG. 2: Compound MC2780 docked to the KDAC1 protein (A) in the *B. malayi* protein and (B) in the *H. sapiens* protein. Compound MC2780 is shown as a stick model along with important residues for ligand binding.
Figure 3:
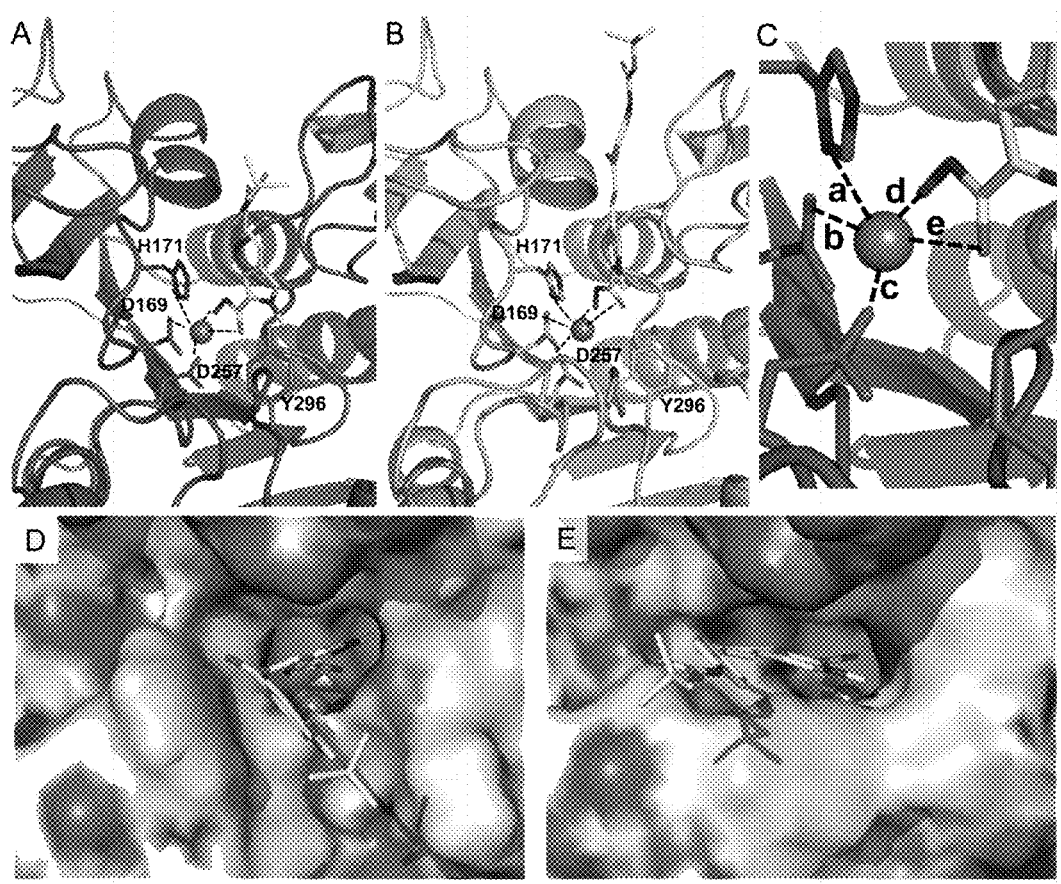
FIG. 3: Compound MC2776 docked to the KDAC1 protein (A) in the *B. malayi* protein and (B) in the *H. sapiens* protein. Compound MC2776 is shown as a stick model along with important residues for ligand binding. (C) shows a close-up view of the zinc-centered square based pyramid. (D) and (E) show the rendered surface models of the representations from (A) and (B).
Figure 4:
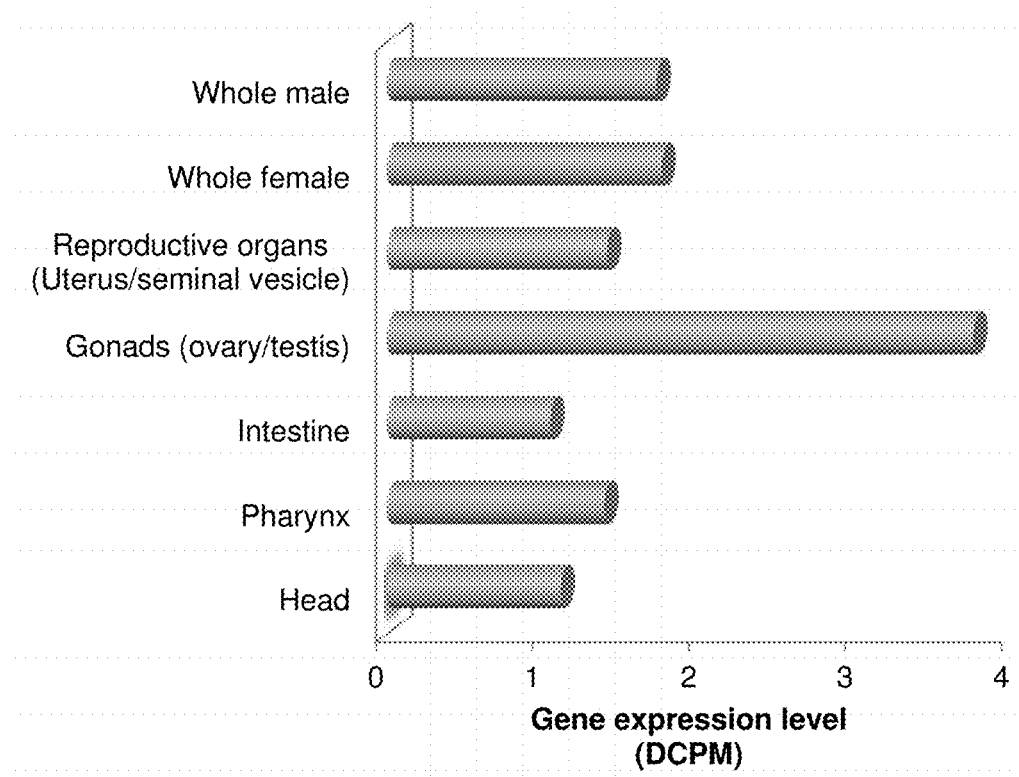
FIG. 4: Expression level of *A. suum* KDAC1 gene (GS 10652) in different tissues.

Two of the representative compounds, MC2780 and MC2776, were docked to the KDAC1 isotypes of the host (human) and each of the parasitic species (*B. malayi*, *L. donovani*, and *P. falciparum*), FIGS. 2 and 3, respectively. The KDAC1 isotype was chosen because it is ubiquitously expressed in all tissues within all the organisms studied, FIG. 4.

Homology models were built for the KDAC1 orthologs from three parasitic species (*B. malayi*, *L. donovani*, and *P. falciparum*) respectively using the human equivalent crystal structure as a template. The sequence identity and similarity between each target and the template are high, especially for the nematode *B. malayi*, suggesting the models should have adequate resolution for the subsequent docking study. The RMSD (root-mean-square-deviation) values for each model after each step in the modeling process remain stable at below 2 Å, indicating that the models show high similarities to the human structure, and that there are only subtle differences in the loop regions and side chain conformations which may lead to differences in binding modes.

To validate our docking procedure, a benchmark docking study was also performed for the crystal structure (PDB code 4BKX), using the bound ligand (acetate ion). The experimental pose was successfully obtained for acetate (RMSD between lowest energy ligand conformation and crystal structure: 0.74 Å). This validates the potential utility of the docking procedure. The subsequent docking of the two ligands from the screening suggests that both ligands could bind relatively well with the orthologs, but shows some differences at the different ortholog binding sites, especially for the nematode-selective ligand MC2776 (FIG. 3). The models showed that when viewed from above, the pyrrole ring of the ligand was almost perfectly in the plane of the hydroxymate in human KDAC1 with the hydroxymate group chelated with catalytic zinc. However, in the *B. malayi* ortholog, the pyrrole ring was rotated counter-clockwise in order to accommodate the tyrosine residue (Y296) at the opening at the binding channel (FIG. 3, A).

The tyrosine residue is conserved across all the KDAC isotypes among almost all organisms. The different orientation of the Y296 in *B. malayi* could be attributed to a nearby point mutation (C254N). The small hydrophobic residue in the other species is tightly packed beneath the binding pocket; while in *B. malayi*, the bulkier, more hydrophilic asparagine led to a propagation of rearrangements of the two strands nearby, resulting in a misaligned tyrosine residue at the protein surface. In contrast, because of the lack of the pyrrole ring, compound MC2780 showed very similar binding modes in the KDAC1 proteins of human and *B. malayi* (FIG. 2). The tert-butylcarbamate group at position 3 of the terminal phenyl ring is extended toward the outer portion of the binding gorge, contacting one of the loops lining the rim of the catalytic tunnel (residues G677-G686), while in the protist proteins, the same group tilted away to the other side of the channel. Without being bound by theory, the different binding modes of compounds MC2780 and MC2776 at KDAC1 may partially explain the different affinities among different organisms.

Although quantitative binding energies cannot be obtained from simple docking simulations, the distances of the catalytic zinc atom to its coordinating atoms from the protein and ligand were measured in all the models for comparison (Tables 2 and 3). In general, the ortholog protein with higher binding affinity with the ligand shows shorter distance (both mean and standard deviation) to the zinc atom for most of the coordinating atoms, to maintain the optimal square-based pyramidal geometry. Docking results showed that both MC2780 and MC2776 could bind the KDAC1 of the protists (*L. donovani* and *P. falciparum*). However, compound MC2776 did not show any efficacy in any of the protists, while compound MC2780 demonstrated pan-parasite potential. Without being bound by theory, compound MC2776 might not have been able to reach its target under assay conditions due to metabolism, transport, or other issues.

TABLE 2

Distances between compound MC2780 and different species within the KDAC1 protein.

| | Compound MC2780 | | | |
| --- | --- | --- | --- | --- |
| Species | H. sapiens | B. malayi | L. donovani | P. falciparum |
| ZN—ND1 (His171) (a) | 3.18 ± 0.47 | 2.80 ± 0.04 | 2.51 ± 0.18 | 2.64 ± 0.12 |
| ZN—O (Asp 169) (b) | 2.26 ± 0.13 | 2.22 ± 0.05 | 2.43 ± 0.03 | 2.39 ± 0.07 |
| ZN—O (Asp257) (c) | 2.68 ± 0.31 | 2.18 ± 0.08 | 2.17 ± 0.08 | 2.18 ± 0.06 |
| ZN—O1 (Ligand) (d) | 2.24 ± 0.29 | 2.08 ± 0.02 | 2.06 ± 0.06 | 2.09 ± 0.05 |
| ZN—O2 (Ligand) (e) | 2.59 ± 0.41 | 2.26 ± 0.05 | 2.83 ± 0.41 | 2.48 ± 0.26 |
| $EC_{50}$ ($IC_{50}$) (mM) | >10 | 4.39 | — | — |

TABLE 3

Distances between compound MC2776 and different species within the KDAC1 protein.

| | Compound MC2776 | | | |
| --- | --- | --- | --- | --- |
| Species | H. sapiens | B. malayi | L. donovani | P. falciparum |
| ZN—ND1 (His171) (a) | 2.76 ± 0.09 | 2.75 ± 0.09 | 2.30 ± 0.05 | 2.66 ± 0.15 |
| ZN—O (Asp169) (b) | 2.12 ± 0.04 | 2.17 ± 0.03 | 2.41 ± 0.02 | 2.46 ± 0.11 |
| ZN—O (Asp257) (c) | 2.44 ± 0.03 | 2.16 ± 0.06 | 2.09 ± 0.09 | 2.20 ± 0.04 |
| ZN—O1 (Ligand) (d) | 2.04 ± 0.01 | 2.11 ± 0.04 | 2.05 ± 0.04 | 2.13 ± 0.08 |
| ZN—O2 (Ligand) (e) | 2.62 ± 0.15 | 3.09 ± 0.08 | 3.10 ± 0.21 | 2.21 ± 0.11 |
| $EC_{50}$ ($IC_{50}$) (mM) | 4.81 | 2.53 | 0.47 | 0.06 |

Example 5

Identification of Active Site Variance of the KDAC Proteins

For each KDAC protein isotype, a representative X-ray structure from its human ortholog was chosen as the structural template. Any residue with an atom within a distance cutoff (10 Å) to the catalytic zinc ion was defined as an active-site residue. Sequence alignments of other parasite orthologs with the human protein (built by MUSCLE for each KDAC family) were used to identify residues that were different in the parasite, and these residues were identified as variants at the active site.

To facilitate selective ligand design, orthologous proteins within the parasite species were systematically examined and variant residues near the active site were also identified for comparison with human protein structures. X-ray crystal structures of the catalytic domain have been reported for 6 of the 11 zinc-containing KDAC isotypes in human, i.e. KDAC1, 2, 3, 8 (class I) and 4, 7 (class II). Among them, KDAC7 lacks a clear ortholog in any of the parasite species, so active-site variants were reported for KDAC1, 2, 3, and 8 together with the only class II isotype KDAC4 (Tables 4 and 5), showing that active-site residues were well conserved in most of parasite orthologs (especially for KDAC1). The kinetoplastid orthologs have slightly more variance, with 8 out of the 50 residues being different from the human protein. All the other orthologs of KDAC1 in the parasite proteins had 5 or fewer residues different from the human protein, with the exception of B. malayi, which had 6 different residues.

TABLE 4

Sequence variations of KDAC proteins of parasitic species in comparison with the hose (H. sapiens)

| Target | | | PDB Code | Total defined residues | Nematode | | | | | | | | | | |
| --- | --- | --- | --- | --- | --- | --- | --- | --- | --- | --- | --- | --- | --- | --- | --- |
| Class | Protein | Human gene | | | Acey | Asuu | Bmal | Cele | Dimm | Hcon | Lloa | Name | Tmur | Tspi | Tsui |
| I | KDAC1 | ENSG00000116478 | 4BKX | 50 | 1 | 1 | 6 | 5 | 2 | 1 | 2 | 1 | 4 | 3 | 3 |
| | KDAC2 | ENSG00000196591 | 4LXZ | 49 | — | 0 | 0 | 3 | 0 | 1 | 0 | 12 | — | — | — |
| | KDAC3 | ENSG00000171720 | 4A69 | 50 | 3 | 3 | 2 | 3 | 4 | 3 | 4 | 3 | 4 | 4 | 3 |
| | KDAC8 | ENSG00000147099 | 1T67 | 48 | — | — | — | — | — | — | — | — | — | — | — |
| IIA | KDAC4 | ENSG00000068024 | 4CBY | 49 | 22 | 5 | 13 | 5 | 6 | 5 | 6 | 5 | 14 | 9 | 13 |

TABLE 5

Sequence variations of KDAC proteins of parasitic species in comparison with the hose (*H. sapiens*)

| Class | Target Protein | Human gene | PDB Code | Total defined residues | Kinetoplastid | | | | Malaria | Trematode | | | |
|---|---|---|---|---|---|---|---|---|---|---|---|---|---|
| | | | | | Tcru | Tbru | Lmaj | Ldon | Pfal | Sman | Sjap | Shem | Csin |
| I | KDAC1 | ENSG00000116478 | 4BKX | 50 | 8 | 8 | 8 | 8 | 3 | 4 | 1 | 1 | 4 |
| | KDAC2 | ENSG00000196591 | 4LXZ | 49 | — | — | — | — | — | — | — | — | — |
| | KDAC3 | ENSG00000171720 | 4A69 | 50 | 21 | 26 | 14 | 14 | — | 3 | 3 | 3 | 6 |
| | KDAC8 | ENSG00000147099 | 1T67 | 48 | — | — | — | — | — | 8 | 8 | 8 | 8 |
| IIA | KDAC4 | ENSG00000068024 | 4CBY | 49 | — | — | — | — | — | 14 | 7 | 9 | 7 |

Among the KDAC proteins compared, one unique residue was identified, C254N. Without being bound by theory, this uniquely different residue may also be a contributing factor to the different binding mode of compound MC2776. Additionally, without being bound by theory, this demonstrates that variations at active sites could play an important role in the pursuit of selective ligands. It is not surprising to see a higher variances for KDAC3 in the kinetoplastids, since each of the two genera have been grouped into its own orthologous protein cluster (*Leishmania* and *Trypanosoma*), suggesting their divergent distance from the human ortholog. KDAC8s of trematodes also clustered into a separate cluster than the mammalian orthologs, but still showed quite high conservation at the active sites, with only 8 out of the 48 residues different. In the class IIA family cluster, only one member was found for the parasites except for *P. falciparum*. Annotated KDAC4 proteins (nematodes and flatworms) were compared with the human KDAC4 structure and were well-conserved except for *A. ceylanicum*, with 22 different residues out of a total of 49. A closer examination revealed that this was due to the fragmented sequence within that region, since at position 21, there are gaps instead of amino acid residues. This is likely an artifact resulted from the draft nature of the genome (proteome) data.

When introducing elements of the present invention or the preferred embodiments(s) thereof, the articles "a", "an", "the" and "said" are intended to mean that there are one or more of the elements. The terms "comprising", "including" and "having" are intended to mean that there may be additional elements other than the listed elements.

In view of the above, it will be seen that the several objects of the invention are achieved and other advantageous results attained.

As various changes could be made in the above compositions and methods without departing from the scope of the invention, it is intended that all matter contained in the above description and shown in the accompanying figures shall be interpreted as illustrative and not in a limiting sense.

What is claimed is:

1. A method for treating a parasitic disease in a subject in need thereof comprising administering to the subject a pharmaceutical composition comprising a therapeutically effective amount of a compound that inhibits lysine deacetylase (KDAC) activity, wherein the parasitic disease is caused by a parasite selected from the group consisting of a nematode, a protist, and a flatworm and wherein the compound has a structure of Formula V or pharmaceutical acceptable salts, solvates, clathrates, prodrugs, or stereoisomers thereof:

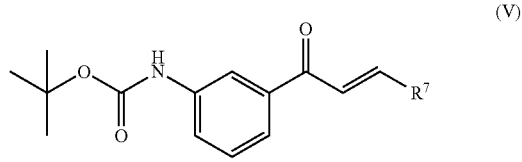

wherein
R[7] in Formula V is -Ph((CH)$_2$C(O)NHOH), or —((C$_4$H$_2$N)(CH$_3$))C(O)NHOH.

2. The method of claim 1 wherein the parasitic disease is caused by a protist.

3. The method of claim 1 wherein the parasitic disease is caused by a nematode.

4. The method of claim 3 wherein the nematode is *Brugia malayi*, *Dirofilaria immitis*, or *Haemonchus contortus*.

5. The method of claim 2 wherein the protist is selected from the group consisting of *Trypanosoma brucei*, *Leishmania donovi*, and *Plasmodium falciparum*.

6. The method of claim 1 wherein the parasitic disease is malaria.

7. The method of claim 1 wherein the compound inhibits the lysine deacetylase activity of at least one isoform selected from the group consisting of KDAC1, KDAC2, KDAC3, KDAC4, KDAC5, KDAC6, KDAC7, KDAC8, KDAC9, KDAC10, KDAC11, and a combination thereof.

8. The method of claim 1 wherein the compound inhibits the lysine deacetylase activity of at least one KDAC isoform with an inhibition activity (IC$_{50}$) from about 10 to about 0.02 nM.

9. The method of claim 1 wherein the subject is a mammal.

10. The method of claim 1 wherein the subject is a human.

11. The method of claim 1 wherein the compound has a structure of

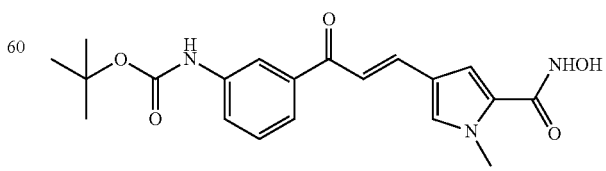

or a pharmaceutically acceptable salt thereof.

12. The method of claim 1 wherein the compound has a structure of
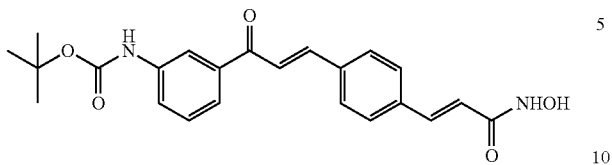
or a pharmaceutically acceptable salt thereof.
* * * * *

UNITED STATES PATENT AND TRADEMARK OFFICE
CERTIFICATE OF CORRECTION

PATENT NO. : 10,154,997 B2
APPLICATION NO. : 15/228802
DATED : December 18, 2018
INVENTOR(S) : Marshall et al.

Page 1 of 1

It is certified that error appears in the above-identified patent and that said Letters Patent is hereby corrected as shown below:

In the Specification

The following Government License Rights Paragraph should be inserted after the title and before the heading "Reference to Related Applications" at Column 1, Line 3:
--GOVERNMENT LICENSE RIGHTS
This invention was made with government support under AI081803 awarded by the National Institutes of Health. The government has certain rights in the invention.--

Signed and Sealed this
Fourth Day of February, 2020

Andrei Iancu
*Director of the United States Patent and Trademark Office*